United States Patent [19]
Bartlett et al.

[11] Patent Number: 5,308,865
[45] Date of Patent: May 3, 1994

[54] 2-CYANO-3-HYDROXY-ENAMIDES

[75] Inventors: Robert R. Bartlett, Darmstadt, Fed. Rep. of Germany; David P. Kay; Elizabeth A. Kuo, both of Swindon, England; Rudolf Schleyerbach, Hofheim am Taunus; Wilfried Schwab, Wiesbaden, both of Fed. Rep. of Germany

[73] Assignee: Roussel Uclaf, France

[21] Appl. No.: 1,564

[22] Filed: Jan. 6, 1993

[30] Foreign Application Priority Data

Jan. 8, 1992 [GB] United Kingdom ................ 9200275

[51] Int. Cl.$^5$ ................ C07C 255/36; A61K 31/275
[52] U.S. Cl. ................................. 514/465; 514/521; 514/522; 549/439; 558/392
[58] Field of Search ............... 558/392; 549/439; 514/465, 521, 522

[56] References Cited
U.S. PATENT DOCUMENTS

| | | | |
|---|---|---|---|
| 4,061,767 | 12/1977 | Ertel et al. | 558/392 X |
| 4,892,963 | 1/1990 | Gallagher et al. | 558/414 |
| 4,965,276 | 10/1990 | Bartlett et al. | 514/521 X |

FOREIGN PATENT DOCUMENTS

| | | |
|---|---|---|
| 2555789 | 7/1977 | Fed. Rep. of Germany . |
| 0484223 | 5/1992 | France . |
| 9117748 | 11/1991 | World Int. Prop. O. . |

*Primary Examiner*—Joseph Paul Brust
*Attorney, Agent, or Firm*—Bierman and Muserlian

[57] ABSTRACT

A compound selected from the group consisting of a compound of the formula

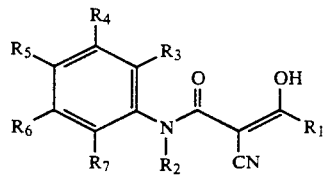

wherein $R_1$ is selected from the group consisting of

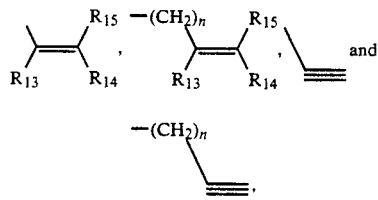

$R_{13}$, $R_{14}$ and $R_{15}$ are individually selected from the group consisting of hydrogen, halogen and alkyl of 1 to 3 carbon atoms, n is an integer from 1 to 3, $R_2$ is hydrogen or alkyl of 1 to 3 carbon atoms, $R_3$, $R_4$, $R_5$, $R_6$ and $R_7$ are individually selected from the group consisting of hydrogen, halogen, —$NO_2$, —CN, alkyl, alkylthio and alkoxy of 1 to 6 carbon atoms, alkylcarbonyl of 2 to 6 carbon atoms, cycloalkyl of 3 to 6 carbon atoms,

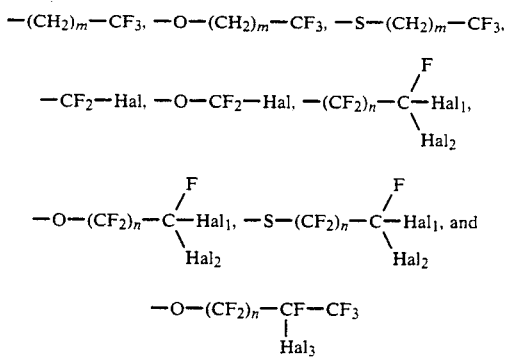

(Abstract continued on next page.)

m is 0, 1, 2 or 3, n is 1, 2 or 3; Hal, Hal$_1$, Hal$_2$ and Hal$_3$ are individually halogen and
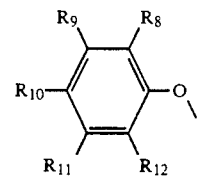
R$_8$, R$_9$, R$_{10}$, R$_{11}$ and R$_{12}$ are individually any of the groups defined above for R$_3$, R$_4$, R$_5$, R$_6$ and R$_7$ or R$_4$ and R$_5$ together form —O—CH$_2$—O— and their non-toxic, pharmaceutically acceptable base addition salts having anti-inflammatory activity.
9 Claims, No Drawings

5,308,865

2-CYANO-3-HYDROXY-ENAMIDES

OBJECTS OF THE INVENTION

It is an object of the invention to provide the novel compounds of formula I and their non-toxic, pharmaceutically acceptable salts and a novel process and intermediates.

It is another object of the invention to provide novel anti-inflammatory compositions and a method of combatting inflammation in warm-blooded animals.

These and other objects and advantages of the invention will become obvious from the following detailed description.

THE INVENTION

The novel compounds of the invention are compounds of the formula

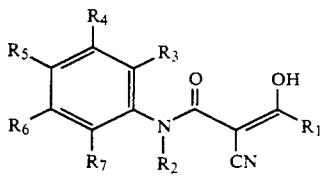

wherein $R_1$ is selected from the group consisting of

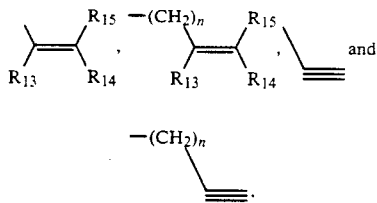

$R_{13}$, $R_{14}$ and $R_{15}$ are individually selected from the group consisting of hydrogen, halogen and alkyl of 1 to 3 carbon atoms, n is an integer from 1 to 3, $R_2$ is hydrogen or alkyl of 1 to 3 carbon atoms, $R_3$, $R_4$, $R_5$, $R_6$ and $R_7$ are individually selected from the group consisting of hydrogen, halogen, $-NO_2$, $-CN$, alkyl, alkylthio and alkoxy of 1 to 6 carbon atoms,

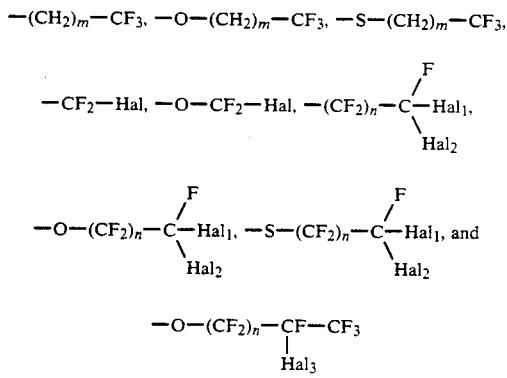

m is 0, 1, 2 or 3, n is 1, 2 or 3; Hal, $Hal_1$, $Hal_2$ and $Hal_3$ are individually halogen and

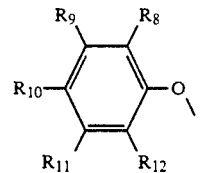

$R_8$, $R_9$ $R_{10}$, and $R_{12}$ are individually any of the groups defined above for $R_3$, $R_4$, $R_5$, $R_6$ and $R_7$ or $R_4$ and $R_5$ together form $-O-CH_213$ $O-$ and their non-toxic, pharmaceutically acceptable base addition salts.

Examples of alkyl of 1 to 3 or 1 to 6 carbon atoms are methyl, ethyl, propyl, isopropyl and linear or branched butyl, pentyl and hexyl. Examples of alkylcarbonyl are acetyl, ethylcarbonyl, propylcarbonyl, butylcarbonyl, isobutylcarbonyl and isopentylcarbonyl.

Examples of cycloalkyl of 3 to 6 carbon atoms are cyclopropyl, cyclobutyl, cyclopentyl and cyclohexyl and examples of alkoxy of 1 to 6 carbon atoms are methoxy, ethoxy, propoxy, isopropoxy butoxy, isobutoxy, pentyloxy an hexyloxy. Alkylthio of 1 to 6 carbon atoms include methylthio, ethylthio, propylthio, isopropylthio and linear or branched butylthio, pentylthio and hexylthio. Halogen includes fluorine, chlorine, bromine and iodine.

The base addition salts can be salts with inorganic or organic bases such as salts formed with mineral bases such as sodium, potassium, lithium, calcium, magnesium and ammonium salts, or salts formed with organic bases such as methylamine, propylamine, trimethylamine,diethylamine, triethylamine,N,N-dimethylethanolamine, tris(hydroxymethyl)-aminomethane,ethanolamine,-pyridine,picoline, dicyclohexylamine, morpholine, benzylamine, procaine, lysine or arginine, histidine and N-methylglucamine.

Among the preferred compounds of formula I are those wherein $R_3$, $R_4$, $R_5$, $R_6$ and $R_7$ are individually selected from the group consisting of hydrogen, fluorine, chlorine, bromine, iodine, methyl, ethyl, t-butyl, methoxy, methylthio, trifluoromethyl, trifluoromethoxy, trifluoromethylthio, pentafluoroethyl, bromodifluoromethoxy, cyano, nitro, phenoxy and p-chlorophenoxy or those wherein $R_4$ and $R_5$ together are $-O-CH_2-O-$, while $R_3$, $R_6$ and $R_7$ are defined above and those wherein $R_2$ is hydrogen or methyl and $R_1$ is an defined above.

Other preferred compounds of formula I are those wherein $R_1$ is selected from the group consisting of

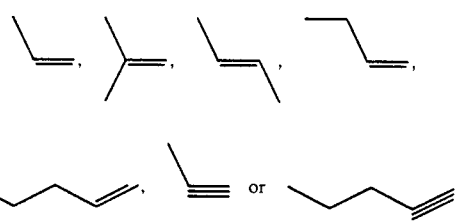

those wherein $R_2$ is hydrogen or methyl; and those wherein $R_3$, $R_4$, $R_5$, $R_6$ and $R_7$ are individually selected from the group consisting of hydrogen, fluorine, chlorine, bromine , methyl, trifluoromethyl, trifluoromethoxy, nitro, cyano and phenoxy.

Especially preferred compounds are 2-cyano-3-hydroxy-4-methyl-N-(4-trifluoromethylphenyl)-penta-2,4-dienamide; 2-cyano-3-hydroxy-N-(4-trifluoromethylphenyl)-hexa-2,5-dienamide; 2-cyano-3-hydroxy-4-methyl-N-(4-chloro-3-trifluoromethylphenyl)-penta-2,4-dienamide; 2-cyano-3-hydroxy-4-methyl-N-(4-trifluoromethoxyphenyl)-penta-2,4-dienamide; 2-cyano-3-hydroxy-4-methyl-N-(4-bromophenyl)-penta-2,4-dienamide; 2-cyano-3-hydroxy-N-(4-trifluoromethylphenyl)-hepta-2-ene-6-ynamide; 2-cyano-3-hydroxy-N-(4-chloro-3-trifluoro-methylphenyl)-hexa-2,5-dienamide; 2-cyano-3-hydroxy-N-(3-methyl-4-trifluoromethylphenyl)-hepta-2,6-dienamide and 2-cyano-3-hydroxy-N-(4-trifluoromethylphenyl)-hepta-2,6-dienamide and their non-toxic, pharmaceutically acceptable base addition salts.

The novel process of the invention for the preparation of a compound of formula I comprises reacting a compound of the formula

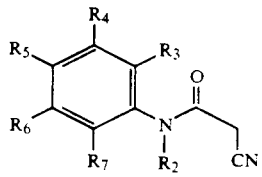

II wherein $R_3$, $R_4$, $R_5$, $R_6$ and $R_7$ are defined above with sodium hydride in the optional presence of a catalyst and then with a compound of the formula

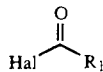

III wherein Hal is halogen and $R_1$ is a defined above or
b) with a compound of the formula

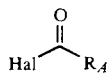

III$_A$ wherein Hal is halogen and $R_A$ is $R_1$ as defined above additionally carrying a protecting group to obtain a compound of the formula

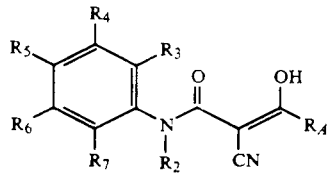

I$_A$ wherein $R_A$, $R_2$, $R_3$, $R_4$, $R_5$, $R_6$ and $R_7$ are as defined above and subsequently cleaving the protecting group to obtain a compound of formula I$_A$ in which $R_A$ is $R_1$ as defined above.

Compounds of formula I wherein $R_1$ is

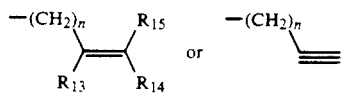

in which $R_{13}$, $R_{14}$ and $R_{15}$ are as defined above and n is 2 or 3 may additionally be prepared by reacting a compound of the formula

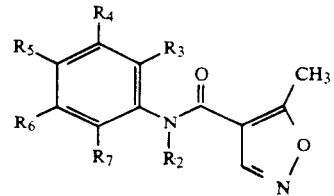

V wherein $R_2$ to $R_7$ are as hereinbefore defined with a compound of the formula

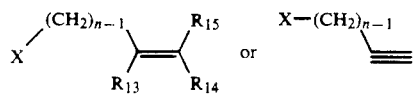

wherein X is a suitable leaving group, preferably iodine, and n, $R_{13}$, $R_{14}$ and $R_{15}$ are as defined above in the presence of a strong base.

The compounds of formula I may be converted into a base addition salt by known means.

The reaction between the compound of formula II and sodium hydride is preferably effected in the presence of an anhydrous organic solvent such as tetrahydrofuran and optionally in the presence of a catalyst which is capable of solvating the sodium hydride such a imidazole. The reaction between the product of the reaction of the compound of formula II and sodium hydride and the compound of formula III or III$_A$ is preferably effected in the presence of an anhydrous organic solvent such as tetrahydrofuran at low temperature. In some cases, the optimum temperature will be in the region of 0° C. and in others, the optimum temperature will be between −80° C. and −50° C.

An example of a compound of formula III is propynoyl fluoride and this may be for example prepared by reaction of propiolic acid with benzoyl fluoride and distilled into the subsequent reaction mixture.

When $R_A$ is $R_1$ additionally carrying a protecting group, this protecting group may be an arylseleno or phenylseleno group. Deprotection of such a protecting group may be carried out by oxidation using a peroxide such as hydrogen peroxide either in the absence of a solvent or in the presence of a mixture of organic solvents such as methanol/dichloromethane.

The reaction between the compounds of formula V and VI or VI' is preferably effected in an anhydrous organic solvent such as tetrahydrofuran at a low temperature. A preferred example of a strong base is butyllithium.

The compounds of formula I are acidic in character and the base addition salts of the compounds of the formula I can advantageously be prepared by reaction with approximately stoichiometric proportions of an inorganic or organic base. The salts can be prepared without intermediate isolation of the corresponding acidic compound.

The compounds of formula II may be prepared by the process of European Patent Application No. 91402890.7 filed on 29 Oct. 1991 by reacting a product of the formula

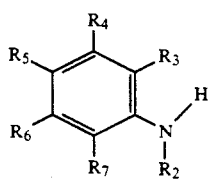

wherein R₂, R₃, R₄, R₅, R₆ and R₇ are as defined above in a process similar to that described by Nohara et al in J. Med. Chem. (1985), Vol. 28 (5), p. 559 to 566 by the following scheme:

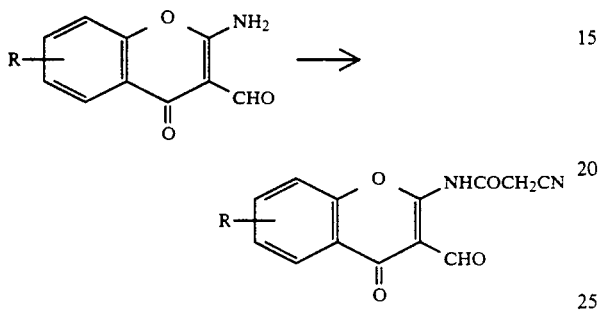

The compounds of formula IV are generally known products or can be prepared by diazotation, reaction of the diazonium salt with an appropriate copper or alkali metal salt (e.q. CuCl, KI, NaCN), then reduction of the corresponding nitroanilines by processes known per se. The nitroanilines used can be prepared as indicated, for example in Sura et al., Synthetic Communications, (1988) Vol. 18 (16–17), page 2161 to 2165.

Certain of the anilines of formula IV can be prepared by processes described in EP-A-206951 or by reduction of the corresponding nitrobenzenes some of which are known. The compounds of formula V are generally known products or can be prepared by a process similar to that described in Patent Application No. WO.91/17748.

The novel anti-inflammatory compositions of the invention are comprised of anti-inflammatorily effective amount of at least one compound of formula I or its non-toxic, pharmaceutically acceptable base salts and an inert pharmaceutical carrier. The compositions may be in the form of tablets, dragees, capsules, granules, suppositories or injectable solutions or suspensions.

The compositions inhibit both the inflammatory response caused by irritant agents, and delayed hypersensitivity reactions, by hindering activation of the immune cells by a specific antigen and are useful for the treatment of rheumatoid arthritis, chronic inflammatory diseases of immune or non-immune origin (e.g. graft-versus-host disease, transplantation reactions, uveitis) and cancer.

Examples of suitable pharmaceutical carriers are talc, arabic gum, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The novel method of the invention for treating inflammation in warm-blooded animals, including humans, comprises administering to warm-blooded animals an anti-inflammatorily effective amount of at least one compound of formula I and its non-toxic, pharmaceutically acceptable base salts. The compounds may be administered orally, rectally or parentally and the usual daily dose is 0.0013 to 2.66 mg/kg depending upon the condition treated, the specific compound and the method of administration.

The novel intermediates of the invention are the compounds of the formula

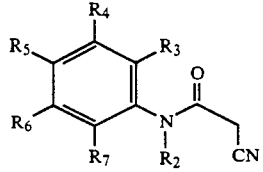

wherein R₂ is as defined hereinbefore and one of R₃, R₄, R₅, R₆ and R₇ is cycloalkyl of 3 to 6 carbon atoms or

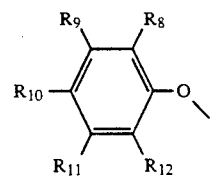

as defined above, the remaining groups being as defined hereinbefore. Specific preferred compounds are [4-(4'-chlorophenoxy) phenyl]-cyanoacetanilide; and [4-(4'-trifluoromethylphenoxy) phenyl]-cyanoacetanilide and 4-trifluoromethoxy-cyanoacetanilide.

In the following examples there are described several preferred embodiments to illustrate the invention. However, it should be understood that the invention is not intended to be limited to the specific embodiments.

EXAMPLE 1

2-cyano-3-hydroxy-4-methyl-N-(4-trifluoromethylphenyl)-penta-2,4-dienamide.

The compound was prepared, from the appropriate starting materials, by a similar method to that described in Example 8 below (method F).

EXAMPLE 2

2-cyano-3-hydroxy-N-(4-trifluoromethyphenyl)-penta-2,4-dienamide (method C).

PREPARATION 1

Step A 7.0 g of 4'-trifluoromethyl-cyanoacentanilide (0.0307 mole) in 200 ml of dry tetrahydrofuran where stirred under nitrogen during the addition of 0.02 g of imidazole as a catalyst and 2.3 g of sodium hydride 80% oil dispersion (0.077 mole) and the suspension was stirred for 2 hours at room temperature. The mixture was cooled to −78° C. and treated dropwise with 9.11 g (0.037 mole) of 3-(phenyl-seleno) propinoyl chloride prepared as described in J. Med. Chem. (1988), Vol. 31, p. 1190 to 1196. The mixture was stirred for 90 minutes at −78° C., was poured onto dilute hydrochloric acid-/ice and filtered. The solid was dissolved in dichloromethane, washed with water, dried over magnesium sulfate and the solvent was removed under reduced pressure. Trituration with diethyl ether gave 13.40 g of 2-cyano-3-hydroxy-5-phenylseleno-N-4-trifluoromethylphenyl)-penta-2,4-dienamide as colorless crystals (99% yield).

Step B 8.0 g (0.018 mole) of 2-cyano-3-hydroxy-5-phenyl-seleno-N-(4-trifluoromethylphenyl)-penta-2,4-dienamide in 200 ml of dichloro-methane was cooled to 0° C. and treated with 4.0 ml of 30% hydrogen peroxide. The mixture was stirred vigorously for 30 minutes to obtain a colorless suspension of the intermediate selenoxide. The mixture was diluted with 40 ml of methanol and 200 ml of dichloro-methane and stirred at room temperature for 1 hour and passed through a column of silica gel. The eluent was concentrated under reduced pressure and diluted with diethyl ether to obtain 2.8 g (54%) of colorless crystals of the expected compound.

EXAMPLE 3

2-cyano-3-hydroxy-4-methyl-N-(4-bromo-3-methylphenyl)-penta-2,4-dienamide (method A).

A solution of 6.3 g of 4'-bromo-3'-methyl-cyanoacetanilide (0.025 mole) in 200 ml of dry tetrahydrofuran was stirred under nitrogen during the addition of 0.02 g of imidazole as a catalyst and 1.85 g (0.0625 mole) of sodium hydride 80% oil dispersion. The suspension was stirred at room temperature for 1 hour, then was cooled to −78° C. 2.95 ml (0.03 mole) of methacryloyl chloride freshly distilled from phenothiazine were added dropwise and the mixture was warmed to −20° C. over 90 minutes. The mixture was poured onto dilute hydrochloric acid/ice, and filtered. The solid was dissolved in dichloromethane, washed with water, dried over magnesium sulfate and evaporated under reduced pressure to obtain 8.0 g (99.7%) of the title compound as colorless crystals.

EXAMPLE 4

2-cyano-3-hydroxy-N-(4-trifluoromethylphenyl)-penta-2,4-dienamide (method E).

5.0 g (0.22 mole) of 4'-trifluoromethyl-cyanoacetanilide in 150 ml of dry tetrahydrofuran were stirred at room temperature under nitrogen and treated with 2.0 g (0.066 mole) of sodium hydride 80% oil dispersion. The suspension was stirred for 1 hour at room temperature and then was cooled to −70° C. The flask was equipped with an acetone/dry ice condenser and used as the collecting flask from a distillation apparatus charged with 3.01 ml (0.05 mole) of propiolic acid and 15 g of benzoyl fluoride (0.12 mole), as described in J.A.C.S. (1974), Vol. 96 (18), p. 5855 to 5859. The distillation flask was heated in an oil bath at 50° C. and the liberated propynoyl fluoride passed via an air condenser directly into the cold solution of the carbanion. The mixture was stirred at −70° C. for 1 hour and was then quenched by pouring onto a mixture of dilute hydrochloric acid/ice. The mixture was extracted with ethyl acetate and the extracts were dried over magnesium sulfate. The solvent was removed under reduced pressure and triuration with diethyl ether gave colorless crystals of the title compound. Chromatography of the mother liquors over silica gel, eluting with dichloromethane isolated 2.49 g (40%) of the remainder of the product.

EXAMPLE 5

(E)-2-cyano-3-hydroxy-N-(4-trifluoromethylphenyl)-hexa-2,4-dienamide (method B).

0 6.0 g (0.026 mole) of 4'-trifluoromethyl-cyanoacetanilide in 200 ml of dry tetrahydrofuran were stirred under nitrogen during the addition of 0.02 g of imidazole and 1.95 g (0.065 mole) of sodium hydride 80% oil dispersion. The suspension was stirred for 2 hours at room temperature and then was cooled to −78° C. before the dropwise addition of 3.06 ml (0.031 mole) of freshly distilled crotonyl chloride. The mixture was stirred at −78° C. for 2 hours, poured onto a mixture of dilute hydrochloric acid/ice and filtered. The solid was dissolved in dichloromethane, washed with water, dried over magnesium sulfate and the solvent was removed under reduced pressure to obtain 7.65 g (99%) of colorless crystals of the expected compound.

EXAMPLE 6

2-cyano-3-hydroxy-N-(4-trifluoromethylphenyl)-hexa-2,5-dienamide (method D).

6.0 g (0.026 mole) of 4'-trifluoromethyl-cyanoacetanilide in 200 ml of dry tetrahydrofuran were stirred under nitrogen at room temperature and were treated with 1.95 g (0.065 mole) of sodium hydride 80% oil dispersion. The mixture was stirred for a further 30 minutes at room temperature and cooled to −50° C. before the dropwise addition of 3.3 g (0.033 mole) of 3-butenoyl chloride prepared as described in J. Chem. Soc. (1948), p. 661. The mixture was stirred at −50° C. for 2 hours, then was poured onto dilute hydrochloric acid/ice and filtered. The solid was chromatographed over silica gel eluting with dichloromethane to give 2.4 g (31%) of the title compound as colorless crystals and 3 g of starting material were recovered.

EXAMPLE 7

2-cyano-3-hydroxy-4-methyl-N-(4-trifluoromethylphenyl)-penta-2,4-dienamide.

The compound was prepared from the appropriate starting materials, by the method of Example 8 below (method F).

EXAMPLE 8

2-cyano-3-hydroxy-4-methyl-N-(4-trifluoromethoxyphenyl)-penta-2,4-dienamide (method F).

A solution of 0.5 g (2.05 mmol) of 4-trifluoromethoxy-cyano-acetanilide in 22 ml of dry THF was stirred under nitrogen at room temperature while a catalytic amount of imidazole and, 0.15 g (5.12 mmol) sodium hydride 80% oil dispersion were added. After 10 minutes, the solution was cooled to −78° C. and 0.24 ml (2.46 mmol) of methacryloyl chloride, freshly distilled from phenolthiazine, was quickly added. After 30 minutes, the reaction was complete. 0.3 ml of glacial acetic acid were added and the mixture was stirred for a further 30 minutes. The mixture was poured into dilute hydrochloric acid at 0° C. and the precipitated product was filtered off, washed with water (3×5 ml) and ether (5 ml), and dried to obtain 575 mg (90%) of the title compound.

EXAMPLE 9

2-cyano-3-hydroxy-4-methyl-N-[4-(4'-chlorophenoxy)-phenyl]-penta-2,4-dienamide.

The compound was prepared from the appropriate starting materials by the method of Example 8 above (method F) except that no imidazole catalyst was used.

EXAMPLE 10

2-cyano-3-hydroxy-4-methyl-N-(4-bromophenyl)-penta-2,4-dienamide

The compound was prepared from the appropriate starting materials by the method of Example 8 above (method F).

EXAMPLE 11

2-cyano-3-hydroxy-4-methyl-N-[4-(4'-trifluoromethylphenoxy)-phenyl]-penta-2,4-dienamide.

The compound was prepared from the appropriate starting materials by the method of Example 8 above (method F).

EXAMPLE 12

2-cyano-3-hydroxy-N-(4-trifluoromethylphenyl)-hepta-2,6-dienamide (method G).

6.75 g (0.025 mol) of 5-methyl-4-(N-(4-trifluoromethyl)-phenyl)carbamoyl-isoxazole were dissolved in 500 ml of absolute tetrahydrofuran under an argon atmosphere and 32 ml of a 2.5 N solution (0.08 mol) of butyllithium in hexane were slowly added at $-78°$ C. After 1.5 hours, 10.8 ml (0.1 mol) of allyliodide were added at that temperature. After an additional 2 hours, 20 ml of water were added and the dry-ice bath was removed. When warmed up near to 0° C., approx. 500 ml of ethyl acetate and 200 ml of 1N HCl were added and after phase separation, the organic layer was washed with water, dried and concentrated. The product was crystallized from acetone/water using a small amount of 1N HCl to obtain 6.35 g of the expected product melting at 145° C.

EXAMPLE 13

2-cyano-3-hydroxy-N-(4-chloro-3-methylphenyl)-hepta-2,6-dienamide.

The compound was prepared starting from 5-methyl-4-(N-(4-chloro-3-methyl)-phenyl)-carbamoyl-isoxazole using the procedure of Example 12 (method G) to obtain 7.5 g of the expected product melting at 134° C.

EXAMPLE 14

2-cyano-3-hydroxy-N-(4-trifluoromethylphenyl)-hepta-2-ene-6-ynamide.

The compound was prepared starting from 5-methyl-4-(N-(4-trifluoromethyl)-phenyl)-carbamoyl-isoxazole using the procedure of Example 12 (method G) and propargyl iodide as alkylating agent to obtain 4.0 g of the expected product melting at 172° C.

EXAMPLE 15

2-cyano-3-hydroxy-N-(4-chloro-3-methylphenyl)-hepta-2-ene-6-ynamide.

The compound was prepared starting from 5-methyl-4-(N-(4-chloro-3-methyl)-phenyl)-carbamoyl-isoxazole using the procedure of Example 12 (method G) and propargyl iodide as alkylating agent to obtain 3.2 g of the expected product melting at 147° C.

The following Examples 16 to 31 were prepared from the appropriate starting materials by either method A or D described above.

EXAMPLE 16

2-cyano-3-hydroxy-4-methyl-N-(4-chlorophenyl)-penta-2,4-dienamide (method A).

EXAMPLE 17

2-cyano-3-hydroxy-4-methyl-N-(4-iodophenyl)-penta-2,4-dienamide (method A).

EXAMPLE 18

2-cyano-3-hydroxy-4-methyl-N-(4-fluorophenyl)-penta-2,4-dienamide (method A).

EXAMPLE 19

2-cyano-3-hydroxy-4-methyl-N-(3-methyl-4-trifluoromethylphenyl)-penta-2,4-dienamide (method A).

EXAMPLE 20

2-cyano-3-hydroxy-4-methyl-N-(4-cyanophenyl)-penta-2,4-dienamide (method A).

EXAMPLE 21

2-cyano-3-hydroxy-4-methyl-N-(4-nitrophenyl)-penta-2,4-dienamide (method A).

EXAMPLE 22

2-cyano-3-hydroxy-N-(4-trifluoromethoxyphenyl)-hexa-2,5-dienamide (method D).

EXAMPLE 23

2-cyano-3-hydroxy-N-(4-trifluoromethylthiophenyl)-hexa-2,5-dienamide (method D).

EXAMPLE 24

2-cyano-3-hydroxy-N-(4-chloro-3-trifluoromethylphenyl)-hexa-2,5-dienamide (method D).

EXAMPLE 25

2-cyano-3-hydroxy-N-(4-fluorophenyl)-hexa-2,5-dienamide (method D).

EXAMPLE 26

2-cyano-3-hydroxy-N-(3,4-difluorophenyl)-hexa-2,5-dienamide (method D).

EXAMPLE 27

2-cyano-3-hydroxy-N-(2,4-difluorophenyl)-hexa-2,5-dienamide (method D).

EXAMPLE 28

2-cyano-3-hydroxy-4-methyl-N-(3-trifluoromethylphenyl)-penta-2,4-dienamide (method A).

EXAMPLE 29

2-cyano-3-hydroxy-4-methyl-N-(3,4-difluorophenyl)-penta-2,4-dienamide (method A).

EXAMPLE 30

2-cyano-3-hydroxy-4-methyl-N-(3-chloro-4-fluorophenyl)-penta-2,4-dienamide (method A).

EXAMPLE 31

2-cyano-3-hydroxy-4-methyl-N-(3,4-dichlorophenyl)-penta-2,4-dienamide (method A).

EXAMPLE 32

2-cyano-3-hydroxy-N-(4-chlorophenyl)-hepta-2,6-dienamide.

The compound was prepared starting from 5-methyl-4-(N-(4-chlorophenyl)-carbamoyl-isoxazole using the procedure of Example 12 (method G) to obtain 4.3 g of the expected product melting at 138° C.

EXAMPLE 33

2-cyano-3-hydroxy-N-(3-methyl-4-trifluoromethylphenyl)-hepta-2,6-dienamide.

The compound was prepared starting from 5-methyl-4-(N-(4-trifluoromethyl-3-methyl)-phenyl)-carbamoyl-isoxazole using the procedure of Example 12 (method G) to obtain 4.29 g of the expected product melting at 133° C.

Spectral data, yields, melting points and analytical data for the examples are given in Table I.

TABLE I

[Structure: Ar-NH-C(=O)-CH(CN)-C(=O)-R₁ ⇌ Ar-NH-C(=O)-C(CN)=C(OH)-R₁]

| Ex | Ar | R₁ | Yield % / Method | m. pt °C. | IR cm⁻¹ KBr | ¹H NMR δ | Formula M. wt | Analysis % Calc. | Analysis % Found |
|---|---|---|---|---|---|---|---|---|---|
| 1 | 4-F₃C-C₆H₄- | CH₂=C(CH₃)- | 69 Method F | 191–193 | 3725(NH), 2220(CN), 1630, 1598, 1541, 1320, 1106, 1062, 832. | CDCl₃ 17.09(1H, s); 7.44(2H, d); 7.21(2H, d); 3.34(3H, s); 2.13(1H, m); 1.26(2H, m); 1.05(2H, m). | $C_{14}H_{11}F_3N_2O_2$ 296.25 | C 56.76 H 3.74 F 19.24 N 9.46 O 10.80 | 56.85 3.82 19.17 9.47 — |
| 2 | 4-F₃C-C₆H₄- | CH₂=CH- | 54 Method C | 206–208 | 3300(NH), 2215(CN), 1632, 1604, 1550, 1530, 1412, 1332, 1321, 1111, 1069, 837. | DMSO-d₆ 12.17(1H, s); 7.81(2H, d); 6.88(2H, d); 6.20(1H, dd); 5.69(1H, dd). | $C_{13}H_9F_3N_2O_2$ 282.22 | C 55.33 H 3.21 F 20.20 N 9.93 O 11.34 | 55.23 3.27 20.27 10.00 — |
| 3 | 2-Br-6-CH₃-C₆H₃- | CH₂=C(CH₃)- | 100 Method A | 143–144 | 3300(NH), 2220(CN), 1608, 1542, 1481, 1357, 1310, 1028, 935. | CDCl₃ 15.90(1H, s); 7.73(1H, s); 7.52(1H, d); 7.39(1H, d); 7.23(1H, dd); 6.04(1H, s); 5.31(1H, s); 2.41(3H, s); 2.08(3H, s). | $C_{14}H_{13}BrN_2O_2$ 321.18 | C 52.36 H 4.08 Br 24.88 N 8.72 O 9.96 | 52.42 4.23 26.90 8.74 — |
| 4 | 4-F₃C-C₆H₄- | HC≡C- | 40 Method E | 170 dec | 3290(NH), 2215(CN), 2109, 1622, 1604, 1324, 1259, 1141, 1100, 1064. | DMSO-d₆ 11.96(1H, s); 7.74(2H, d); 7.62(2H, d); 4.23(1H, s). | $C_{13}H_7F_3N_2O_2$ 280.21 | C 55.72 H 2.52 F 20.34 N 10.00 O 11.42 | 55.41 2.63 20.35 9.99 — |
| 5 | 4-F₃C-C₆H₄- | CH₃-CH=CH- | 99 Method B | 210–220 subl. | 3315(NH), 2219(CN), 1650, 1631, 1610, 1565, 1555, 1330, 1160, 1118, 1072, 842. | DMSO-d₆ 11.24(1H, s); 9.15(1H, s); 7.84(2H, d); 7.72(2H, d); 6.97(1H, sxt); 6.55(1H, dd); 1.99(3H, dd). | $C_{14}H_{11}F_3N_2O_2$ 296.25 | C 56.76 H 3.74 F 19.24 N 9.46 O 10.80 | 56.40 3.88 18.82 9.42 — |

TABLE I-continued

| Ex | Ar | R₁ | Yield % | m. pt °C. | IR cm⁻¹ KBr | ¹H NMR δ | Formula M. wt | Analysis % Calc. | Analysis % Found |
|---|---|---|---|---|---|---|---|---|---|
| 6 | F₃C-C₆H₄- | CH₂CH₂CH=CH₂ | 31 Method D | 166–168 | 3300(NH), 2215(CN), 1629, 1588, 1552, 1381, 1322, 1163, 1120, 1071, 848. | CDCl₃ 15.49(1H, s); 7.93(1H, s); 7.64(4H, s); 5.90(1H, m); 5.33(2H, m); 3.38(3H, d). | $C_{14}H_{11}F_3N_2O_2$ 296.25 | C 56.76 H 3.74 F 19.24 N 9.46 O 10.80 | C 56.71 H 3.79 F 19.07 N 9.50 — |
| 7 | 4-Cl-3-CF₃-C₆H₃- | C(CH₃)=CH₂ | 63 Method F | 159 | 3280(NH), 2205(CN), 1620, 1580, 1550, 1510, 1478, 1450, 1350, 1312, 1300, 1260, 1221, 1170, 1130, 1026, 950, 932, 893, 878, 820. | DMSO-d₆ 12.05(1H, s); 8.28(1H, m); 7.72(2H, m); 5.40(1H, s); 5.33(1H, s); 1.93(3H, s.) | $C_{14}H_{10}ClF_3N_2O_2$ 330.70 | C 50.85 H 3.05 Cl 10.72 F 17.23 N 8.47 O 9.68 | C 50.99 H 3.11 — — N 8.53 — |
| 8 | F₃CO-C₆H₄- | C(CH₃)=CH₂ | 90 Method F | 156 | 2290, 2210, 1630, 1610, 1550, 1500, 1450, 1410, 1370, 1298, 1110, 960, 935, 910, 835, 805, 780. | DMSO-d₆ 11.38(1H, s); 7.70(2H, d); 7.36(2H, d); 6.04(1H, s); 5.55(2H, d); 1.97(1H, d). | $C_{14}H_{11}F_3N_2O_3$ 312.25 | C 53.85 H 3.55 F 18.25 N 8.97 O 15.37 | C 54.07 H 3.72 — N 8.96 — |
| 9 | 4-Cl-C₆H₄-O-C₆H₄- | C(CH₃)=CH₂ | 58 Method F | 115–116 | 3270, 2214, 1602, 1580, 1549, 1502, 1483, 1454, 1416, 1370, 1317, 1298, 1289, 1249, 1229, 1163, 1088, 1008, 843, 823. | CDCl₃ 2.09(3H, s); 5.68(1H, s); 6.04(1H, s); 6.95(2H, d+v, J=9.2Hz); 7.31(2H, d+v, J=9.0Hz); 7.46(2H, d+v, J=9.0Hz); 7.75(1H, br s); 15.97 (1H, s). | $C_{19}H_{15}ClN_2O_3$ 354.80 | C 64.32 H 4.26 Cl 9.99 N 7.90 O 13.53 | C 64.41 H 4.33 Cl 9.98 N 7.90 O 13.38 |

TABLE I-continued

| Ex | Ar | R₁ | Yield % | m. pt °C. | IR cm⁻¹ KBr | ¹H NMR δ | Formula M. wt | Analysis % Calc. | Analysis % Found |
|---|---|---|---|---|---|---|---|---|---|
| 10 | 4-Br-C₆H₄ | isopropenyl (H₃C) | 65 Method F | 148 | 3300, 2220, 1875, 1635, 1480, 1450, 1400, 1370, 1310, 1285, 1240, 1172, 1107, 1065, 1005, 935, 910, 809, 780, 767. | DMSO-d₆ 11.08(1H, s); 7.54(4H, m); 5.62(2H, d); 1.98(3H, s). | C₁₃H₁₁BrN₂O₂ 307.15 | C 50.84 H 3.61 Br 26.00 N 9.12 O 10.42 | C 51.20 H 3.67 — N 8.79 — |
| 11 | 4-(4-F₃C-C₆H₄-O)-C₆H₄ | isopropenyl (H₃C) | 69 Method F | 155 | 3272, 2214, 1604, 1552, 1501, 1367, 1333, 1316, 1290, 1253, 1233, 1196, 1170, 1156, 1115, 1102, 1060, 1012, 834. | CDCl₃ 2.09(3H, s); 5.68(1H, s); 6.05(1H, s); 7.03–7.51(2H, d, J=8.80Hz); 7.59(2H, d, J=8.60Hz); 7.78(1H, s, NH); 15.93 (1H, s, OH). | C₂₀H₁₅N₂O₃F₃ 388.35 | C 61.86 H 3.89 N 7.21 O 12.36 F 14.68 | C 61.73 H 3.95 N 7.19 O 12.60 F 14.53 |
| 12 | 4-F₃C-C₆H₄ | pentenyl | 82 Method G | 145 | 3300(NH), 2220(CN), 1630, 1590, 1555, 1415, 1390, 1315, 1265, 1190, 1165, 1130, 1117, 1070, 1010, 845. | DMSO-d₆ 2.25–2.7(4H, m); 4.98–5.15(2H, m); 5.88(1H, m); 7.65 and 7.78(4H, AA'BB'); 11.2 (1H, s). | C₁₅H₁₃N₂O₂F₃ 310.28 | C 58.07 H 4.22 N 9.03 O 10.31 F 18.37 | |
| 13 | 2-CH₃,4-Cl,?-C₆H₃ | pentenyl | 66 Method G | 134 | 3300(NH), 2215(CN), 1590, 1550, 1480, 1310, 1045, 990, 920, 865, 820, 810. | DMSO-d₆ 2.25–2.7(7H, m); 4.95–5.15 (2H, m); 5.85(1H, m); 7.27–7.55 (3H, m); 10.7(1H, s). | C₁₅H₁₅N₂O₂Cl 290.75 | C 61.97 H 5.20 N 9.63 O 11.01 Cl 12.19 | |

TABLE I-continued $$\underset{H}{Ar-N}\underset{O}{\overset{O}{\parallel}}\underset{CN}{\overset{R_1}{\underset{|}{C}}}\underset{O}{\overset{O}{\parallel}}R_1 \rightleftharpoons \underset{H}{Ar-N}\underset{O}{\overset{O}{\parallel}}\underset{CN}{\overset{OH}{\underset{\parallel}{C}}}R_1$$

| Ex | Ar | R₁ | Yield % | m. pt °C. | IR cm⁻¹ KBr | ¹H NMR δ | Formula M. wt | Analysis % Calc. | Found |
|---|---|---|---|---|---|---|---|---|---|
| 14 | F₃C—⟨C₆H₄⟩— | —CH₂CH₂CH=CH₂ (pentenyl) | 52 Method G | 172 | 3310(NH), 2220(CN), 1630, 1590, 1555, 1415, 1325, 1160, 1120, 1070, 840. | DMSO-d₆ 2.5 and 2.75 (2H each, m); 2.85(1H, t, J=2.5Hz); 7.64 and 7.78(4H, AA'BB'); 1.15(1H, s). | C₁₅H₁₁N₂O₂F₃ 308.26 | C 58.45<br>H 3.60<br>N 9.09<br>O 10.38<br>F 18.49 | |
| 15 | 2-CH₃,3-Cl-C₆H₃— | pentenyl | 44 Method G | 147 | 3310(NH), 2220(CN), 1610, 1600, 1590, 1555, 1490, 1315, 825. | DMSO-d₆ 2.29(3H, s); 2.5 and 2.74 (2H each, m); 2.85(1H, t, J=2.5Hz); 7.28–7.55 (3H, m); 10.8(1H, s). | C₁₅H₁₃N₂O₂Cl | C 62.40<br>H 4.54<br>N 9.70<br>O 11.08<br>Cl 12.28 | |
| 16 | 4-Cl-C₆H₄— | CH₂=C(CH₃)— | 85 Method A | 149–151 | 3300(NH), 2210(CN), 1890, 1650, 1495, 1460, 1415, 1380, 1325, 1295, 1250, 1180, 1120, 1100, 1095. | DMSO-d₆ 11.00(1H, s); 7.60(2H, m); 7.43(2H, m); 5.64(2H, d); 1.98(3H, s). | C₁₃H₁₃N₂O₂Cl 262.83 | C 59.44<br>H 4.22<br>N 10.69<br>Cl 13.49 | 59.06<br>4.26<br>10.50<br>13.53 |
| 17 | 4-I-C₆H₄— | CH₂=C(CH₃)— | 68 Method A | 154–157 | 3300(NH), 2230(CN), 1620, 1590, 1560, 1530, 1480, 1465, 1390, 1360, 1310, 1285, 1230, 1110, 1060. | DMSO-d₆ 11.46(1H, s); 7.61(2H, d); 7.44(2H, d); 5.48(2H, d); 1.94(3H, s). | C₁₃H₁₁N₂O₂I 354.15 | C 44.09<br>H 3.13<br>N 7.91<br>I 35.83 | 43.90<br>3.14<br>7.81<br>35.67 |

TABLE I-continued $$\text{Ar}-\underset{H}{N}-\overset{O}{\underset{\|}{C}}-\underset{CN}{\overset{|}{CH}}-\overset{O}{\underset{\|}{C}}-R_1 \rightleftharpoons \text{Ar}-\underset{H}{N}-\overset{O}{\underset{\|}{C}}-\underset{CN}{\overset{\|}{C}}=\underset{R_1}{\overset{OH}{C}}$$

| Ex | Ar | R₁ | Yield % Method | m. pt °C. | IR cm⁻¹ KBr | ¹H NMR δ | Formula M. wt | Analysis % Calc. | Analysis % Found |
|----|----|----|----------------|-----------|-------------|----------|---------------|------------------|------------------|
| 18 | 4-F-C₆H₄ | CH₂=C(CH₃)– | 70 Method A | 111–112 | 3310(NH), 2210(CN), 1880, 1690, 1620, 1550, 1505, 1460, 1415, 1370, 1320, 1270, 1220, 1155, 1100, 1015, 940, 830. | DMSO-d₆ 11.05(1H, s); 7.57(2H, m); 7.19(2H, m); 5.60(2H, d); 1.95(3H, s). | C₁₃H₁₁N₂O₂F 246.24 | C 63.41 H 4.50 N 11.38 | 63.50 4.80 10.96 |
| 19 | 3-CF₃-4-CH₃-C₆H₃ | CH₂=C(CH₃)– | 84 Method A | 147–149 | 3280(NH), 2190(CN), 1635, 1600, 1530, 1440, 1390, 1350, 1300, 1250, 1230, 1140, 1110, 1090, 1030, 820. | DMSO-d₆ 11.50(1H, s); 7.62(3H, d); 5.48(2H, d); 2.45(3H, s); 1.97(1H, s). | C₁₅H₁₃N₂O₂F₃ 310.27 | C 58.07 H 4.22 N 9.03 O 10.31 F 18.37 | |
| 20 | 4-NC-C₆H₄ | CH₂=C(CH₃)– | 77 Method A | 175–177 | 3290(NH), 2220(CN), 1915, 1695, 1600, 1580, 1550, 1460, 1415, 1380, 1330, 1310, 1280, 1250, 1190, 1110, 1015. | DMSO-d₆ 12.29(1H, s); 7.75(4H, s); 5.35(2H, d); 1.92(3H, s). | C₁₄H₁₁N₃O₂ 253.26 | C 66.40 H 4.38 N 16.59 O 12.63 | |
| 21 | 4-O₂N-C₆H₄ | CH₂=C(CH₃)– | 85 Method A | 208–210 | 3320(NH), 2200(CN), 1635, 1610, 1560, 1500, 1340, 1305, 1245, 1180, 1105, 990, 940, 850. | DMSO-d₆ 12.48(1H, s); 8.22(2H, d); 7.80(2H, d); 5.37(2H, d); 1.92(3H, s). | C₁₃H₁₁N₃O₄ 273.24 | C 57.14 H 4.06 N 15.38 | 56.97 4.20 15.20 |

TABLE I-continued

| Ex | Ar | R₁ | Yield % Method | m. pt °C. | IR cm⁻¹ KBr | ¹H NMR δ | Formula M. wt | Analysis % Calc. | Analysis % Found |
|---|---|---|---|---|---|---|---|---|---|
| 22 | F₃CO–C₆H₄– | CH₂CH=CH₂ (allyl) | 70 Method D | 148–150 | 3280(NH), 2185(CN), 1596, 1578, 1545, 1495, 1280, 1190, 1130. | CDCl₃ 15.60(1H, s); 7.68(1H, s); 7.52(2H, m); 7.24(2H, d); 5.93(1H, m); 5.32(2H, m); 3.37(2H, d). | $C_{14}H_{11}N_2O_3F_3$ 312.26 | C 53.85 H 3.55 N 8.97 F 18.25 | C 53.89 H 3.61 N 8.99 F 18.24 |
| 23 | F₃CS–C₆H₄– | CH₂CH=CH₂ | 73 Method D | 145–147 | 3260(NH), 2187(CN), 1590, 1580, 1568, 1530, 1478, 1391, 1368, 1303, 1279, 1170, 1142, 1120, 1110, 1072. | CDCl₃ 15.52(1H, s); 7.74(1H, s); 7.60(4H, m); 5.94(1H, m); 5.34(1H, d, J=15.8Hz); 5.30(1H, d, J=10.2Hz); 3.38(2H, d, J=6.8Hz). | $C_{14}H_{11}N_2O_2SF_3$ 328.32 | C 51.22 H 3.38 N 8.53 S 9.76 | C 51.46 H 3.37 N 8.65 S 9.66 |
| 24 | 2-Cl-5-CF₃-C₆H₃– | CH₂CH=CH₂ | 61 Method D | 160–162 | 3301(NH), 2224(CN), 1629, 1587, 1551, 1487, 1381, 1323, 1177, 1144, 1132. | CDCl₃ 15.42(1H, s); 7.90(1H, d, J=2.6Hz); 7.82(1H, s); 7.69(1H, m); 7.51(1H, d, J=8.6Hz); 5.89(1H, m); 5.31(2H, m); 3.38(2H, d, J=6.8Hz). | $C_{14}H_{10}N_2O_2F_3Cl$ 330.70 | C 50.85 H 3.05 N 8.47 Cl 10.72 F 17.24 | C 50.79 H 3.09 N 8.44 Cl 10.71 F 17.28 |
| 25 | F–C₆H₄– | CH₂CH=CH₂ | 55 Method D | 129–131 | 3320(NH), 2218(CN), 1595, 1568, 1513, 1418, 1385, 1321, 1267, 1217, 835. | CDCl₃ 15.72(1H, s); 7.64(1H, s); 7.45(2H, m); 7.10(2H, m); 5.89(1H, m); 5.31(2H, dd, J=15.6, 11Hz); 3.37(2H, d, J=6.6Hz). | $C_{13}H_{11}N_2O_2F$ 246.24 | C 63.41 H 4.50 N 11.38 F 7.72 | C 63.37 H 4.57 N 11.44 F 7.82 |

TABLE I-continued

| Ex | Ar | R₁ | Yield % | m. pt °C. | IR cm⁻¹ KBr | ¹H NMR δ | Formula M. wt | Analysis % Calc. | Analysis % Found |
|---|---|---|---|---|---|---|---|---|---|
| 26 | 2,4-difluorophenyl | CH₂CH=CH₂ (allyl-like, CH₂-CH=CH-CH₃? shown as -CH₂-CH=CH-) | 48 Method D | 135-136 | 3289(NH), 2220(CN), 1599, 1564, 1518, 1439, 1391, 1290, 1252, 1217. | CDCl₃ 15.52(1H, s); 7.56(2H, m); 7.13(2H, m); 5.89(1H, m); 5.30(2H, m); 3.37(2H, dd, $J=17, 9.8Hz$); 3.37(2H, d, $J=6.8Hz$). | $C_{13}H_{10}N_2O_2F_2$ 264.23 | C 59.09 H 3.81 N 10.60 F 14.38 | C 59.08 H 3.89 N 10.62 F 14.44 |
| 27 | 2-fluoro-6-fluorophenyl | (allyl chain) | 38 Method D | 68-69 | 3297(NH), 2226(CN), 1597, 1562, 1510, 1385, 1262, 966, 933. | CDCl₃ 15.40(1H, s); 7.99(1H, m); 7.67(1H, m); 6.93(2H, m); 5.93(1H, m); 5.35(2H, dd, $J=16.8, 11Hz$); 3.38(2H, d, $J=6.8Hz$). | $C_{13}H_{10}N_2O_2F_2$ 264.23 | C 59.09 H 3.81 N 10.60 F 14.38 | C 59.39 H 3.97 N 10.47 F 13.98 |
| 28 | 3-(trifluoromethyl)phenyl | CH₂C(CH₃)=CH₂ | 76 Method A | 131-3 | 3302(NH), 2214(CN), 1640, 1551, 1497, 1370, 1324, 1275, 1171, 1128. | CDCl₃ 15.80(1H, s); 7.99(1H, s); 7.87(1H, m); 7.69(1H, m); 7.48(2H, m); 6.05(1H, s); 5.69(1H, s); 2.09(3H, s). | $C_{14}H_{11}N_2O_2F_3$ 296.26 | C 56.76 H 3.74 N 9.45 F 19.24 | C 56.67 H 3.82 N 9.43 F 19.21 |
| 29 | 2,4-difluorophenyl | CH₂C(CH₃)=CH₂ | 65 Method A | 155-6 | 3310(NH), 2212(CN), 1642, 1561, 1518, 1441, 1373, 1290. | CDCl₃ 15.78(1H, s); 7.84(1H, s); 7.56(1H, m); 7.16(2H, m); 6.03(1H, m); 5.69(1H, m); 2.09(3H, t, $J=1.0Hz$). | $C_{13}H_{10}N_2O_2F_2$ 264.23 | C 59.09 H 3.81 N 10.60 F 14.38 | C 58.91 H 3.85 N 10.59 F 14.41 |

TABLE I-continued

| Ex | Ar | R₁ | Yield % | m. pt °C. | IR cm⁻¹ KBr | ¹H NMR δ | Formula M. wt | Analysis % Calc. | Analysis % Found |
|---|---|---|---|---|---|---|---|---|---|
| 30 | 4-F, 3-Cl phenyl | H₂C=C(CH₃)– | 83 Method A | 198–200 | 3291(NH), 2212(CN), 1638, 1603, 1547, 1503, 1368. | CDCl₃ 15.73(1H, s); 7.71(2H, m); 7.30(2H, m); 6.05(1H, s); 5.69(1H, m); 2.09(1H, s). | $C_{13}H_{10}N_2O_2ClF$ 280.68 | C 55.63<br>H 3.59<br>N 9.98<br>Cl 12.63<br>F 6.77 | 55.47<br>3.63<br>9.96<br>12.89<br>6.70 |
| 31 | 3,4-diCl phenyl | H₂C=C(CH₃)– | 83 Method A | 181–3 | 3302(NH), 2220(CN), 1636, 1607, 1568, 1539, 1479, 1368, 1310, 953, 939. | CDCl₃ 15.71(1H, s); 7.82(1H, s); 7.78(1H, d, J=2.4Hz); 7.44(1H, d, J=8.6Hz); 7.30(1H, dd); 6.05(1H, s); 5.70(1H, m); 2.09(3H, s). | $C_{13}H_{10}N_2O_2Cl_2$ 297.14 | C 52.55<br>H 3.39<br>N 9.43<br>Cl 23.86 | 52.46<br>3.45<br>9.42<br>23.92 |
| 32 | 4-Cl phenyl | CH₂=CH–CH₂–CH₂– | 62 Method G | 138 | 3290(NH), 2220(CN), 1600, 1590, 1560, 1550, 1390, 1310, 1090, 1010, 830. | DMSO-d₆ 2.25–2.7 (4H, m); 4.95–5.17 (2H, m); 5.85(1H, mc); 7.38 and 7.58(4H, AA'BB'); 10.6(1H, s). | $C_{14}H_{13}N_2O_2Cl$ 262.72 | C 60.77<br>H 4.74<br>N 10.12<br>O 11.56<br>Cl 12.81 | |
| 33 | 2-CF₃, 4-CH₃ phenyl | CH₂=CH–CH₂–CH₂– | 53 Method G | 133 | 3300(NH), 2220(CN), 1595, 1555, 1410, 1305, 1160, 1120, 1045, 840. | DMSO-d₆ 2.25–2.65 (7H, m); 4.95–5.15 (2H, m); 5.85(1H, m); 7.7–7.63 (3H, m); 11.3(1H, s). | $C_{16}H_{15}N_2O_2F_3$ 324.30 | C 59.26<br>H 4.66<br>N 8.64<br>O 9.87<br>F 17.57 | |

EXAMPLE 34

Tablets were prepared from 20 mg of the Compound of Example 1 or Example 2 and sufficient excipient of lactose, starch, talc, magnesium stearate for a weight of 150 mg.

PHARMACOLOGICAL ACTIVITY

Test 1: Carrageenan rat paw oedema (PO-R)

One hour after the oral administration of the test compounds or control vehicle to groups 6 to 12 of rats (male CFHB, weight range 160 to 180 g), 1 mg of carrageenan dissolved in 0.2 ml of saline was injected into the right hind foot pad. Contralateral paws received control saline injections and the paw oedema responses were assessed three hours later.

Test 2: Delayed type hypersensitivity mouse paw oedema (DTH-M)

Groups of 8 to 10 mice (male CD-1, weight range 25 to 30 g) were sensitized by the subcutaneous injection of 1 mg of methylated bovine serum albumin (MBSA) in 0.2 ml of volumes of saline/Freund's complete adjuvant (FCA) emulsion. Negative control groups received injections of saline/FCA emulsion. DTH paw oedema responses were assessed twenty-four hours after the right hind foot pad challenge with 0.1 mg of MBSA in 0.5 ml volumes of saline on day seven after sensitization. Contralateral paws received control saline injections. The test compounds or control vehicles were orally administered daily on days four, five, six and twice on day seven, one hour before and six hours after MBSA challenge.

Test 3: Delayed-type hypersensitivity raw paw oedema (DTH-R)

Groups of 8 to 12 rats (male CFHB, weight range 160 to 180 g) were sensitized by the subcutaneous tail base injection of 0.1 ml volumes of FCA. Negative control groups received injections of Freund's incomplete adjuvant. DTH paw oedema responses were assessed twenty-four hours after the right hind foot pad challenge with 0.1 mg of MBSA in 0.4 mg of Mycobacterium tuberculosis extract antigen in 0.2 ml volumes of saline on day seven after sensitization. Contralateral paws received control saline injections. The test compounds were orally administered daily on days four, five, six and twice on day seven, one hour before and six hours after antigenic challenge.

The results of these tests are given in Table II where the percentage inhibition of oedema formation is given. Doses are given in units of mg/kg p.o.

TABLE II

| Example | Test 1 % inhibition | Dose | Test 2 % inhibition | Dose | Test 3 % inhibition | Dose |
|---|---|---|---|---|---|---|
| 1 | 31 | (50) | 54 | (100) | 78 | (50) |
| 2 | 16 | (50) | 7 | (100) | 65 | (50) |
| 3 | 30 | (50) | 36 | (100) | 20 | (50) |
| 4 | −24 | (50) | 45 | (100) | 4 | (50) |
| 5 | 23 | (50) | 50 | (100) | 16 | (50) |
| 6 | 30 | (50) | 75 | (30) | 79 | (50) |
| 7 | 43 | (50) | 62 | (100) | 65 | (50) |
| 8 | 23 | (50) | 60 | (100) | 92 | (50) |
| 9 | 12 | (50) | 44 | (100) | 64 | (50) |
| 10 | 24 | (50) | 61 | (100) | 41 | (50) |
| 11 | 24 | (50) | 26 | (100) | 33 | (10) |
| 12 | −3 | (10) | 43 | (30) | 43 | (10) |
| 13 | 24 | (50) | 62 | (100) | −10 | (50) |
| 14 | 14 | (10) | 66 | (30) | 28 | (10) |
| 15 | — | — | — | — | — | — |
| 16 | 8 | (50) | 17 | (100) | 62 | (50) |
| 17 | −24 | (50) | 15 | (100) | 60/39 | (50) |
| 18 | 15 | (50) | 19 | (100) | 9 | (50) |
| 19 | 39 | (50) | 55/62 | (100) | 24 | (50) |
| 20 | 7 | (50) | 47 | (100) | 26 | (50) |
| 21 | −5 | (50) | 16 | (100) | 30 | (50) |
| 22 | 11 | (50) | 16 | (30) | 78 | (50) |
| 23 | 22 | (50) | 23 | (30) | 62 | (50) |
| 24 | — | — | 64 | (30) | 78 | (50) |
| 25 | 24 | (50) | Toxic | (100) | 46 | (50) |
| 26 | 39 | (50) | Toxic | (100) | 54 | (50) |
| 27 | 14 | (50) | 6 | (100) | 7 | (50) |
| 28 | 39 | (50) | 20 | (100) | 13 | (50) |
| 29 | 39 | (50) | 18 | (100) | 34 | (50) |
| 30 | — | — | 52 | (100) | 37 | (50) |
| 31 | — | — | 53 | (100) | 66 | (50) |
| 32 | — | — | — | — | — | — |
| 33 | — | — | — | — | — | — |

Various modifications of the products and method of the invention may be made without departing from the spirit or scope thereof and it is to be understood that the invention is intended to be limited only as defined in the appended claims.

what is claimed is:

1. A compound selected from the group consisting of a compound of the formula

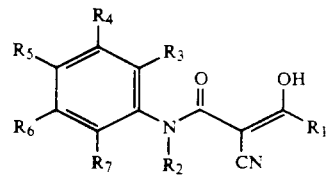

wherein $R_1$ is selected from the group consisting of

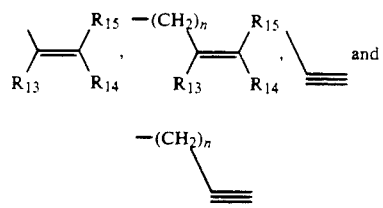

$R_{13}$, $R_{14}$ and $R_{15}$ are individually selected from the group consisting of hydrogen, halogen and alkyl of 1 to 3 carbon atoms, n is an integer from 1 to 3, $R_2$ is hydrogen or methyl, $R_3$, $R_4$, $R_5$, $R_6$ and $R_7$ are individually selected from the group consisting of hydrogen, or fluorine, chlorine, bromine, iodine, methyl, ethyl, t-butyl, methoxy, methlthio, trifluoromethyl, trifluoromethoxy, trifluoromethylthio, pentafluoroethyl, bromodiflurormethoxy, cyano, nitro, phenoxy, trifluoromethylphenoxy, or p-chlorophenoxy group or $R_4$ and $R_5$ together form —O—$CH_2$—O— and their non-toxic, pharmaceutically acceptable base addition salts.

2. A compound of claim 1 wherein $R_1$ is selected from the group consisting of

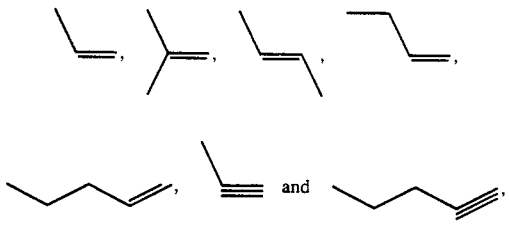

R$_2$ is hydrogen or methyl and R$_3$, R$_4$, R$_5$, R$_6$ and R$_7$ are individually selected from the group consisting of hydrogen, fluorine, chlorine bromine, methyl, trifluoromethyl, trifluoromethoxy, nitro, cyano and phenoxy.

3. A compound of claim 1 selected from the group consisting of 2-cyano-3-hydroxy-4-methyl-N-(4-trifluoromethylphenyl)-penta-2,4-dienamide;
2-cyano-3-hydroxy-N-(4-trifluoromethylphenyl)-hexa-2,5-dienamide;
2-cyano-3-hydroxy-4-methyl-N-(4-chloro-3-trifluoromethylphenyl)-penta-2,4-dienamide;
2-cyano-3-hydroxy-4-methyl-N-(4-trifluoromethoxyphenyl)-penta-2,4-dienamide;
2-cyano-3-hydroxy-4-methyl-N-(4-bromophenyl)-penta-2,4-dienamide;
2-cyano-3-hydroxy-N-(4-trifluoromethylphenyl)-hepta-2-ene-6-ynamide;
2-cyano-3-hydroxy-N-(4-chloro-3-trifluoromethylphenyl)-hexa-2,5-dienamide;
2-cyano-3-hydroxy-N-(3-methyl-4-trifluoromethylphenyl)-hepta-2,6-dienamide; 2-cyano-3-hydroxy-N-(4-trilfuoromethylphenyl)-hepta-2,6-dienamide and their non-toxic, pharmaceutically acceptable base addition salts.

4. An anti-inflammatory composition comprising an anti-inflammatorilly effective amount of at least one compound of claim 1 and an inert pharmaceutical carrier.

5. A composition of claim 4 wherein R$_1$ is selected from the group consisting of

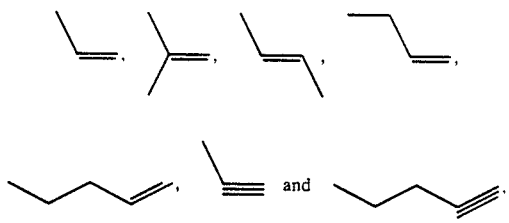

R$_2$ is hydrogen or methyl and R$_3$, R$_4$, R$_5$, R$_6$ and R$_7$ are individually selected from the group consisting of hydrogen, fluorine, chlorine bromine, methyl, trifluoromethyl, trifluoromethoxy, nitro, cyano and phenoxy.

6. A composition of claim 4 wherein the active compound is selected from the group consisting of 2-cyano-3-hydroxy-4-methyl-N-(4-trifluoromethylphenyl)-penta-2,4-dienamide;
2-cyano-3-hydroxy-N-(4-trifluoromethylphenyl)-hexa-2,5-dienamide;
2-cyano-3-hydroxy-4-methyl-N-(4-chloro-3-trifluoromethylphenyl)-penta-2,4-dienamide;
2-cyano-3-hydroxy-4-methyl-N-(4-trifluoromethoxyphenyl)-penta-2,4-dienamide;
2-cyano-3-hydroxy-4-methyl-N-(4-bromophenyl)-penta-2,4-dienamide;
2-cyano-3-hydroxy-N-(4-trifluoromethylphenyl)-hepta-2-ene-6-ynamide;
2-cyano-3-hydroxy-N-(4-chloro-3-trifluoromethylphenyl)-hexa-2,5-dienamide;
2-cyano-3-hydroxy-N-(3-methyl-4-trifluoromethylphenyl)-hepta-2,6-dienamide;
2-cyano-3-hydroxy-N-(4-trifluoromethylphenyl)-hepta-2,6-dienamide and their non-toxic, pharmaceutically acceptable base addition salts.

7. A method treating inflammation in warm-blooded animals comprising administering to warm-blooded animals an anti-inflammatorilly effective amount of at least one compound of claim 1.

8. A method of claim 7 wherein R$_1$ is selected from the group consisting of

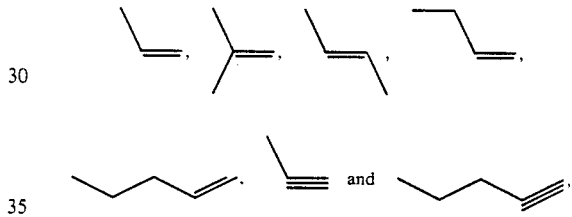

R$_2$ hydrogen or methyl and R$_3$, R$_4$, R$_5$, R$_6$ and R$_7$ are individually selected from the group consisting of hydrogen, fluorine, chlorine bromine, methyl, trifluoromethyl, trifluoromethoxy, nitro, cyano and phenoxy.

9. A method of claim 7 wherein the active compound is selected from the group consisting of 2-cyano-3-hydroxy-4-methyl-N-(4-trifluoromethylphenyl)-penta-2,4-dienamide;
2-cyano-3-hydroxy-N-(4-trifluoromethylphenyl)-hexa-2,5-dienamide;
2-cyano-3-hydroxy-4-methyl-N-(4-chloro-3-trifluoromethylphenyl)-penta-2,4-dienamide;
2-cyano-3-hydroxy-4-methyl-N-(4-trifluoromethoxyphenyl)-penta-2,4-dienamide;
2-cyano-3-hydroxy-4-methyl-N-(4-bromophenyl)-penta-2,4-dienamide;
2-cyano-3-hydroxy-N-(4-trifluoromethylphenyl)-hepta-2-ene-6-ynamide;
2-cyano-3-hydroxy-N-(4-chloro-3-trifluoromethylphenyl)-hexa-2,5-dienamide;
2-cyano-3-hydroxy-N-(3-methyl-4-trifluoromethylphenyl)-hepta-2,6-dienamide;
2-cyano-3-hydroxy-N-(4-trifluoromethylphenyl)-hepta-2,6-dienamide and their non-toxic, pharmaceutically acceptable base addition salts.

* * * * *